United States Patent [19]

Fukuda et al.

[11] Patent Number: 4,939,083
[45] Date of Patent: Jul. 3, 1990

[54] CARBOHYDRATE SPECIFIC TO CHRONIC MYELOGENOUS LEUKEMIA GRANULOCYTES

[75] Inventors: Minoru Fukuda; Michiko Fukuda, both of San Diego, Calif.

[73] Assignee: La Jolla Cancer Research Foundation, La Jolla, Calif.

[21] Appl. No.: 924,935

[22] Filed: Oct. 30, 1986

[51] Int. Cl.$^5$ .................... G01N 33/53; A61K 39/00; C07H 5/04; C07G 37/00
[52] U.S. Cl. ............................ 435/7; 424/9; 424/85.9; 435/240.27; 436/548; 436/813; 530/387; 536/55.1; 536/53
[58] Field of Search ............ 436/548, 811, 813, 501; 435/7, 68, 172.2, 240.22; 530/387, 403, 396, 355, 380, 351; 536/55.1, 53; 935/107, 108, 110; 424/85.9, 9

[56] References Cited

U.S. PATENT DOCUMENTS

| | | | |
|---|---|---|---|
| 4,348,376 | 9/1982 | Goldenberg | 424/1 |
| 4,444,744 | 4/1984 | Goldenberg | 424/1.1 |
| 4,599,305 | 7/1986 | Witte et al. | 435/7 |
| 4,687,733 | 8/1987 | Trewyn et al. | 435/7 |

OTHER PUBLICATIONS

Fukuda et al, The Journal of Biological Chemistry, vol. 260, No. 2, Jan. 1985, pp. 1067-1082.
Sevier et al, Clin. Chem., vol. 27, 1981, pp. 1797-1806.
Fukushi et al, The J. of Biological Chemistry, vol. 259, No. 16, Aug. 25, 1984, pp. 10511-10517.
Houghton et al, PNAS, U.S.A., vol. 82, Feb. 1985, pp. 1242-1246.
Fukuda et al, The Journal of Biological Chemistry, vol. 261, 1986, pp. 2376-2383.
Fukuda et al, The Journal of Biological Chemistry, vol. 260, 1985, pp. 12957-12967.
T. F. Bumol, Q. C. Wang, R. A. Reisfeld and N. O. Kaplan: Monoclonal Antibody and an Antibody-Toxin Conjugate to a Cell Surface Proteoglycan of Melanoma Cells Suppress in Vivo Tumor Growth, Proc. Natl. Acad. Sci., U.S.A., vol. 80, pp. 529-533, 1/83, Immunology.

Primary Examiner—Robert J. Warden
Assistant Examiner—Florina B. Hoffer
Attorney, Agent, or Firm—Pretty, Schroeder, Brueggemann & Clark

[57] ABSTRACT

A substantially purified carbohydrate is provided which is isolated from chronic myelogenous leukemia cells. The carbohydrate is immunogenic and can be utilized to raise both polyclonal and monoclonal antibodies.

17 Claims, 2 Drawing Sheets

CARBOHYDRATE SPECIFIC TO CHRONIC MYELOGENOUS LEUKEMIA GRANULOCYTES

BACKGROUND OF THE INVENTION

This invention relates generally to the area of carbohydrate chemistry and more specifically to unique carbohydrates specific to cancer cells.

Cancer is currently the second leading cause of death in the United States. As a result, substantial efforts have been directed towards developing methods to detect and combat malignancies. However, because cancer affects many different types of cells, separate diagnostic and therapeutic methods must be established for individual cancers. Unique cell surface markers, or biochemical moieties, present on the membranes of particular malignant cells are of import as indicators of a particular type of cancer. The determination of specific cell surface markers potentially permits the targeting of therapeutics specific to malignant cells. Tumor specific cell surface markers have previously been identified for certain cancers of the colon and reproductive tract.

CML is a malignancy of certain cells of the blood system characterized by excessive levels of granulocytes in the peripheral blood. Currently there are some 6,000 new cases in the United States per year. Radiation exposure has been implicated as one causative factor for CML, making the disease of particular concern in connection with contamination from nuclear accidents. While the chronic phase of CML may persist for some years, eventually the disease transforms into an acute stage characterized by aggressive leukemia. Once a patient enters the acute phase, the prognosis is poor, with less than 20 percent surviving one year. Because chemotherapy undertaken during the chronic phase appears to be more effective than that begun after the condition has become acute, early detection is important. The effectiveness of such therapy is hindered, however, because the chemical agents used destroy normal myeloid cells as well as malignant ones.

Thus there is a great and long-felt need for a chemical marker which is specific to cells exhibiting CML but is absent on their normal counterparts. In addition to aiding in the understanding of CML, such a marker would be potentially useful in, for example, both the early diagnosis as well as the specific treatment of the malignancy. The present invention satisfies these needs and provides other related advantages as well.

SUMMARY OF THE INVENTION

The present invention provides a novel carbohydrate which is advantageously used as a marker for chronic myelogenous leukemia. This novel carbohydrate will be hereinafter termed "CML-G2." Because this novel carbohydrate, CML-G2, is apparently absent in normal granulocytes and acute myelogenous leukemia cells, it is a specific marker for CML cells. Moreover, CML-G2 is immunogenic and can therefore be used to produce antibodies which recognize and specifically bind this novel carbohydrate. In another aspect of the invention, antibodies specific to CML-G2 are utilized, for example, in diagnosis and therapy. Such antibodies are produced either polyclonally or monoclonally. Alternatively, other carbohydrate binding proteins, such as lectins, which bind specifically to CML-G2 structure may be used in the same manner as monoclonal antibodies.

In accordance with the present invention, there is provided a purified carbohydrate, CML-G2, having the structure:

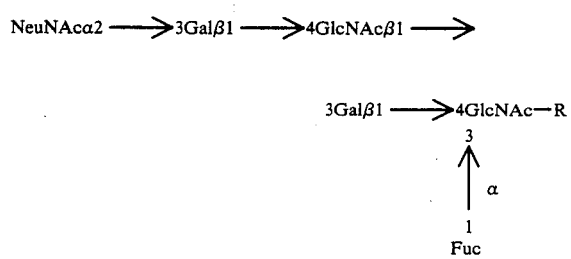

CML-G2 may be characterized as a sialyated fucosyl glycolipid or, more specifically, a polylactosamino lipid. The glycolipid is isolated from granulocytic cells in patients having CML through techniques involving column chromatography, high performance liquid chromatography, and high performance thin layer chromotography. The structure of CML-G2 is unique in that a fucose is attached to the internal N-acetyl glucosamine but not to the subterminal N-acetyl glucosamine. Antibodies specific to this polylactosamino lipid express differential affinity to this polylactosamino lipid than to others because of this unique structure.

It will be appreciated from the foregoing that the present invention provides a novel carbohydrate which is a marker for CML. With this carbohydrate, antibodies can be raised which render possible an immunoassay for the disease. Moreover, the antibodies, together with cytotoxic mechanisms such as complement or specialized lymphocytes, or when conjugated with a toxin, may specifically target the malignant cells for destruction allowing one to avoid deleterious effects on normal cells.

Other features and advantages of the present invention will become apparent from the following more detailed description which illustrates, by way of example, the principles of the invention.

DETAILED DESCRIPTION OF THE PREFERRED EMBODIMENT

In accordance with the invention, a novel carbohydrate termed "CML-G2" is disclosed comprising the structure:

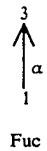

This unique carbohydrate has been found associated with cells from CML patients and is therefore a specific quantitative marker for CML. It is useful, alone or in conjunction with antibodies recognizing it, in the diagnosis and treatment of CML. The abbreviations used herein are presented in Table I.

TABLE I

| | |
|---|---|
| CML | Chronic myelogenous leukemia |
| Gal | Galactose |
| Glc | Glucose |
| Cer | Ceramide |
| NeuNAc | N-acetyl neuraminic acid |
| GlcNAc | N-acetyl glucosamine |
| HPLC | High performance liquid chromatography |
| HPTLC | High performance thin-layer chromatography |
| FAB-MS | Fast atom bombardment mass spectroscopy |
| Fuc | Fucose |
| PBS | Phosphate buffered saline |
| ELISA | Enzyme-linked immunosorbent assay |

Figure 1:
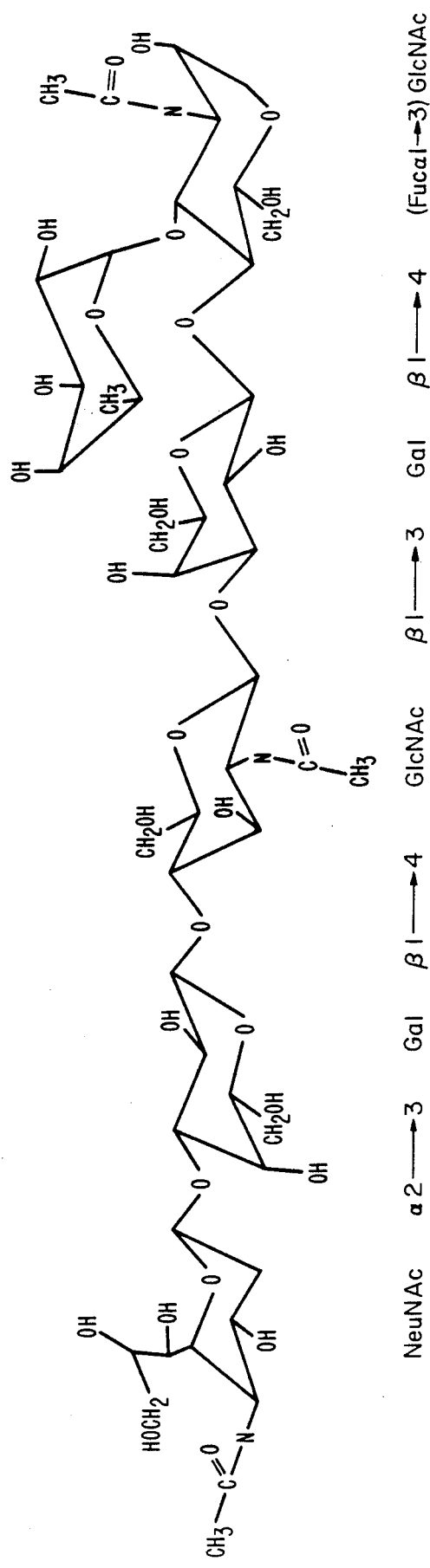
FIG. 1 depicts the chemical structure of CML-G2.
Figure 2:
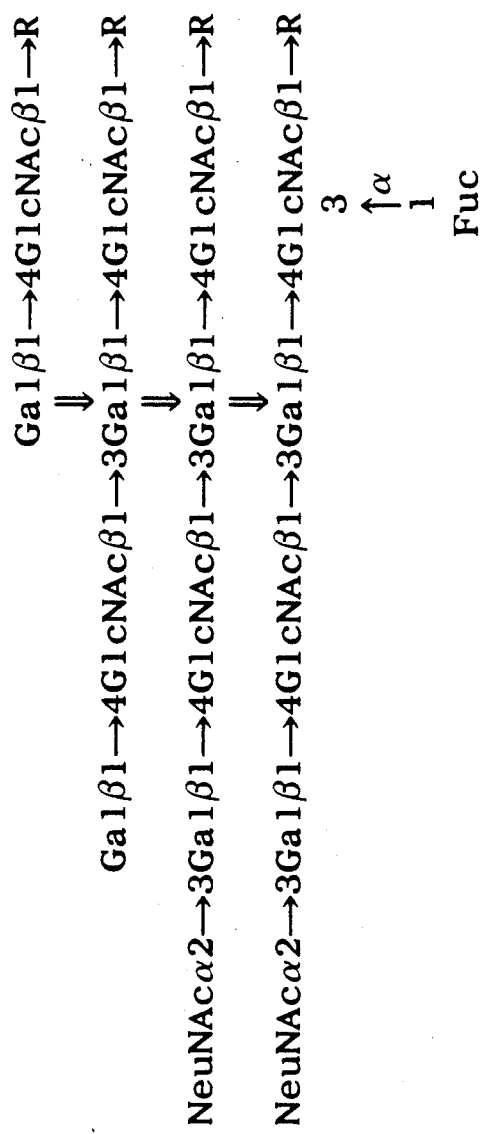
FIG. 2 depicts the suggested biosynthetic pathway by which CML-G2 is formed.

The structure of CML-G2 is shown in FIG. 1. A fucose side group is linked to the internal N-acetyl glucosamine, which is distal to the non-reducing end, rather than to the subterminal N-acetyl glucosamine as in previously known structures. The presence of N-acetyl neuraminic acid at the non-reducing terminal may hamper the addition of fucose to the subterminal N-acetyl glucosamine. While not wishing to be bound by this explanation, it is believed that the structure suggests that CML-G2 is formed by the pathway indicated in FIG. 2. The internal fucose suggests that sialylation precedes fucosylation. If fucosylation were to take place prior to sialylation (addition of N-acetyl neuraminic acid), fucose should be preferentially added at the subterminal N-acetyl glucosamine as seen in neutral glycolipids, but not in CML-G2.

In its native form, the R group of CML-G2 is
1→3Galβ1→5Glcβ1→1Cer
to give the overall structure:

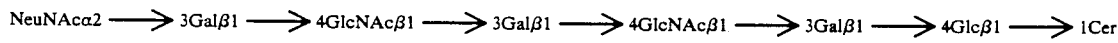

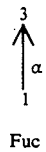

However, the immunogenic specificity of the carbohydrate is preserved where R is H. Additionally, other substituents may replace the native moiety without a loss of immunogenic specificity.

CML-G2 was isolated, as described in greater detail below, from granulocytic cells obtained from patients in the chronic phase of CML. Blood samples from patients were subjected to leukophoresis and hypotonic lysis in order to obtain a granulocyte enriched sample. The glycolipids were then extracted from these cells, fractionated, and further purified. Thin layer chromotography of the acidic glycolipids revealed a doublet unique to CML granulocytes. Further analysis by the methods detailed below revealed that the structure of this carbohydrate is:

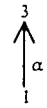

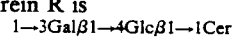

wherein R is
1→3Galβ1→4Glcβ1→1Cer

CML-G2 is immunogenic and is used to raise antibodies either monoclonally or polyclonally. Such antibodies are utilized for both diagnosis and therapy according to conventional methods known to those skilled in the art, including but not limited to direct and competitive immunoassays, including RIA and ELISA, radio imaging, immuno-toxin therapy, and radio-immuno therapy.

The methods used are presented in the following publications which are incorporated herein by reference in their entirety: Fukuda, 1986, J. Biol. Chem. 261:2376 and Fukuda, 985, J. Biol. Chem. 260:1067.

EXAMPLE I

ISOLATION OF HUMAN CELLS

Leukocytes were obtained from adult donors by leukophoresis with an IBM 2997 Blood Cell Separator (NCI-IBM, Endicott, NY). Granulocytes were purified from this mixed leukocyte preparation by dextran sedimentation and Ficoll-Hypaque gradient centrifugation. The Wright-stained smears of the preparation showed that over 95% of the cells were neutrophilic granulocytes.

EXAMPLE II

EXTRACTION OF GLYCOLIPIDS FROM GRANULOCYTES

Human granulocytes (approximately $10^{11}$ cells, 100 ml of packed cells) were extracted with 20 volumes of chloroform/methanol (2:2, 1:1, and 1:2, v/v). After Folch's phase partition, the lower-layer glycolipids were freed from cholesterol and phospholipids by acetylation procedures. Deacetylated lower-phase glycolipids were subjected to QAE-Sephadex A-25 column chromatography and neutral and acidic glycolipids were separated by using the solvent systems described by Ando and Yu (1977, J. Biol. Chem., 252:6247). Upper-layer glycolipids were also separated into neutral and acidic fractions in the same manner.

EXAMPLE III

PURIFICATION OF ACIDIC GLYCOLIPIDS

Acidic glycolipids were purified by high performance liquid chromatography with a Varian HPLC apparatus (Model 5000, Varian Associates, Palo Alto, Calif.). The glycolipids dissolved in a minimum amount of chloroform/methanol (2:1, v/v) were applied to a column (0.4×50 cm) of Iatrobeads (IRS 8010, 10 μm diameter, Iatron, Tokyo, Japan). The column was equilibrated with isopropyl alcohol/hexane/water (55:40:5), eluted over 20 minutes by a gradient to isopropyl alcohol/hexane/water (55:35:10), and followed by a shallower gradient to isopropyl alcohol/hexane/water (55:29:16) over an additional 180 min. The flow rate was constant at 0.5 ml/min and the eluate was collected every 2 minutes. Glycolipids in each tube were analyzed by HPTLC (Si-HPF, J. T. Baker Chemical Co., Phillipsberg, N.Y.) using a solvent system chloroform/methanol/3.5M NH4OH (60:35:8, v/v). The elution positions of glycolipids were as follows: $G_1$, 70–72 min; $G_2$, 72–74 min; $G_3$ 77–86 min; $G_4$, 82–88 min. Each glycolipid fraction recovered was then acetylated in pyridine/acetic anhydride (1:1, v/v). Acetylated glycolipids were then separated on HPTLC (Si-HPF, J. T. Baker) using a solvent of dichloroethane/acetone/water (50:50:1, v/v/v).

Acetylated glycolipids detected by iodine vapor were eluted from thin layer plates and deacetylated with sodium in methanol. Glycolipids obtained were further purified by HPLC in the same manner as described above, with the solvent system as follows. The solvent gradient was programmed as isopropyl alcohol/hexane/water (55:40:5 to 55:37:8) over 10 minutes followed by the gradient to isopropyl alcohol/hexane/water (55:29:16) over 70 minutes. The flow rate was constant at 0.5 ml/min and the eluate was collected every 1 minute. Glycolipids in each tube were analyzed by HPTLC as described above. The elution positions of glycolipids were as follows: $G_1$, 33 min; $G_2$, 34–37 min; $G_3$, 37–39 min; $G_4$, 40–42 min. $G_2$ was selected for further characterization.

EXAMPLE IV

METHYLATION ANALYSIS

The glycolipids were methylated by the method of Hakomori (1964, J. Biol. Chem. (Tokyo) 55:205). The permethylated samples were purified by LH-20 column chromatography and further purified by partition with chloroform/water (1:1, v/v) and the chloroform layer was washed four times with water.

The permethylated samples obtained were then subjected to FAB-MS for sequence analysis. In order to obtain the information on linkages between monosaccharides, the permethylated samples were subjected to acid hydrolysis with 0.5N $H_2SO_4$ in 90% acetic acid at 80° C. for 4 hours. The hydrolysates were then neutralized and acetylated. The alditol acetates of partially methylated sugars were analyzed by gas liquid chromatography mass-spectrometry with a modification in column temperature.

Methylation analysis of $G_2$ produced 1 mol of 2,3,4-tri-O-methylfucose, 3 mol of 2,4,6-tri-O-methylgalactose, 1 mol of 6-O-methyl-N-acetyl glucosamine, 1 mol of 3,6-di-O-methyl-N-acetyl glucosamine, and 1 mol of 2,3,6-tri-O-methylglucose.

EXAMPLE V

FAST ATOM BOMBARDMENT-MASS-SPECTROMETRY (FAB-MS)

FAB-MS was carried out on a VG analytical ZAB HF mass spectrometer (Imperial College, London) according to the method of Fukuda, 1984 J. Biol. Chem. 259:4782, which is incorporated by reference. About 100 to 20 μg of glycolipids were permethylated and about 10 to 20 μg of each derivative were loaded onto the glyceral/thioglyceral matrix for each FAB-MS run.

FAB-MS analysis of permethylated G2 provided the molecular ion $NeuNAc_1.Fuc_1.HexNAc_2.Hex_4.Cer_{16:0}$ (m/z 2421) and $NeuNAc_1.Fuc_1.HexNAc_2.Hex_4.Cer_{18:0}$ (m/z 2449). The same analysis provided fragment ions corresponding to $NeuNAc.Fuc\ HexNAc_2.Hex_3{}^+$(m/z 1652), $NeuNAc.Fuc.Hex_2.HexNAc_2{}^+$(m/z 1448), NeuNAc.Hex.HexNAc.Hex$^+$(m/z 1029), and NeuNAc.-Hex.HexNAc.(m/z 825). If CML-$G_2$ has a fucose residue at the subterminal N-acetyl glucosamine residue, the fragment ion of m/z 999 should be prominent, but fragment ion of m/z 999 was barely detected, indicating that $G_2$ has a sequence of NeuNAc→Hex→HexNAc→Hex→(Fuc→)HexNAo→Hex→Hex→Cer. In addition, the fragment ion of m/z 2183 corresponds to the M-$C_{16:0}$ acyl chain (2421−238) or M-$C_{18:0}$ (2449−266), confirming that the ceramide is composed of the sphingosine with $d_{18:1}$ as the long-chain base and the $C_{16:0}$ and $C_{18:0}$ as the major fatty acids.

EXAMPLE VI

DIGESTION OF GLYCOLIPIDS

Glycolipids were digested with endo-β-galactosidase purified from *Escherichia freundii*. Hydrolysis was carried out under condition 1 (125 milliunits/ml) or condition 2 (1.25 units/ml). After hydrolysis, the sample was partitioned by chloroform/methanol/ water (4:2:1) and the water and organic solvent layers were analyzed by HPTLC for released oligosaccharides and for degraded glycolipids, respectively. β-Galactosidase and β-N-acetylglucosaminidase were purified from Jack bean meal. α-L-fucosidase from bovine kidney was purchased from Boehringer Mannheim, Indianapolis, Ind. The glycolipid sample was incubated with 0.02-0.03 units of the exoglycosidase in 10 μl of 0.05M sodium citrate buffer, pH 4.3, which contains 10 μg of sodium taurodeoxycholate at 37° C. for 24 hours. For β-galactosidase digestion, a condition was chosen under which CTH (Galα1→4Galβ1→4Glc→Cer) was not hydrolyzed to avoid the effect of contaminated α-galactosidase activity. The digest was then dried under nitrogen, dissolved in a chloroform/methanol (2:1, v/v) solution, and analyzed by HPTLC.

$G_2$ was sequentially digested with clostridial neuraminidase, β-galactosidase, and β-N-acetylglucosaminidase. The product was reacted with anti-Lex monoclonal antibody, Pm-81, and gave a positive spot at the same position of the $N_1$-glycolipid, Galβ1→4-(Fucα1→3) GlcNAcβ1→3Galβ1→4Glcβ1→1Cer, whereas the starting material did not react with the same antibody. These results indicate the following structure for G2:

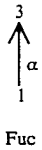

Fuc

Endo-β-galactosidase from *Escherichia freundii* hydrolyzed $G_2$ glycolipid to produce CMH (Glcβ1→1Cer) and a large oligosaccharide. Endo-β- galactosidase cannot hydrolyze the β-galactosidic linkage adjacent to the fucosylated N-acetyl glucosamine. This result is also consistent with the above structure and with synthesis of CML-G2 proceeding as diagrammed in FIG. 2.

EXAMPLE VII

PREPARATION OF CML-G2 SPECIFIC POLYCLONAL ANTIBODIES

Antibodies specific to CML-G2 are raised in mammals such as rabbits, goats, or mice. In the preferred embodiment, ten- week-old female Balb/c mice are injected intravenously with 5 μg CML-G2 in PBS containing 20 μg of *Salmonella minnesota*. The mice are boosted every 4 days with 5 μg CML-G2 in PBS containing 20 μg of *Salmonella minnesota* for a total of seven boosts. Serum is obtained 4 days after the final boost.

In the ELISA, CML-G2 and four control carbohydrates are dissolved in ethanol which contains lecithin and cholesterol. The final concentrations of glycolipid, lecithin and cholesterol are 1 mg/1, 5 mg/1 and 3 mg/1, respectively. Aliquots of 25 μl of antigen are distributed to each well of 96 well polyvinyl chloride microtiter plates and left at room temperature to dry. The plates are stored dessicated at 4° C. until needed. Nonspecific binding sites are blocked with 2% ovalbumin in Tris buffered saline containing 0.2 percent Tween-20 and 0.01 percent Thimerosal, pH 8.0 (TBTT). Fifty μl of appropriate dilutions of primary antibodies are added to the blocked test wells and incubated at room temperature for 30 minutes. Unbound antibodies are removed by washing the wells with freshly deionized $H_2O$ followed by TBTT. Bound primary antibody is detected by a second antibody, horseradish peroxidase conjugated goat anti-mouse antibodies (Capell Co., Cochranville, Pa.). The second antibody is diluted according to manufacturer's recommendation and 50 μl aliquots added to test wells. These are incubated at room temperature for 30 minutes and washed as before. O-Phenylenediamine in 80 mM citrate-phosphate buffer, pH 6.5 is used as substrate for the conjugated peroxidase. Visible reaction products are quantified with an automated microtiter plate reader set at 92 nm. The mouse serum with the highest titer against CML-G2 was designated anti-CML-G2 and was used for all further work.

EXAMPLE VIII

PREPARATION OF CML-G2 SPECIFIC MONOCLONAL ANTIBODIES

Hybridomas producing antibodies against CML-G2 are generated by standard murine fusion procedures as detailed in Kohler and Milstein (Nature, 1975, 256:495), which is incorporated by reference and (Nudelmon 1986, J. Biol. Chem., 261:5487). Briefly, two Balb/c mice immunized with CML-G2 are sacrificed and the spleens removed. Mixed splenocytes are obtained by pressing the spleens through a 30 mesh stainless steel screen. Alternatively, the spleen cells cultured in dishes are reacted in vitro with CML-G2. These are fused with murine or other mammalian myeloma cells (aminopterin sensitive) at a fusion ratio of 10:1 in 35% polyethylene-glycol. These cells are plated out 96 well tissue culture plates in the presence of $2 \times 10^6$ thymocytes/ml. Hybridomas are selected for by growing the cells in the presence of aminopterin poisoned Dulbecco's modified Eagle's media augmented with hypoxanthine, thymine and 10% fetal bovine serum. Hybridomas are screened for reactivity against CML-G2 via ELISA as described above. Positive clones are expanded and subcloned twice. Aliquots of the clones are stored in liquid nitrogen. Supernatants from positive clones are produced in large quantities for further purification of monoclonal antibodies. The specificity of the monoclonal antibodies are determined as described in Example IX.

EXAMPLE IX

ENZYME-LINKED IMMUNOSORBANT ASSAY USING CML-G2

Glycolipids are separated by thin-layer chromatography using a solvent system of chloroform/methanol/ 3.5M NH4 (60:35:8, v/v/v). The reactivity of monoclonal antibodies with glycolipids in a thin-layer plate is directly determined by using the method described by Magnani (1982, J. Biol. Chem., 257:14365), which is incorporated by reference, or alternatively using the Magnani method with the following modifications. The thin-layer plates are first immersed in phosphate buffered saline (PBS) which contains 1% polyvinylpyrolidone and 1% bovine serum albumin. The plates are then exposed to monoclonal antibodies properly diluted in PBS and the secondary antibody, goat anti-mouse IgG, coupled to horseradish peroxidase (Bio Rad, Richmond, Calif.) diluted 1:1000 in PBS. The plates are then washed and exposed to 400 µg/ml O-phenylene diamine (Sigma, St. Louis, Mo.) in 80 mM citrate-phosphate buffer, pH 5.0 containing $H_2O_2$ (Eastman Kodak Chemicals, Rochester, N.Y.) for 15 min. The TLC plate is dried at 56° C. for 30 min and the color reaction determined by suitable means. Alternatively, the secondary antibody, rabbit anti-mouse immunoglobin is added, washed and then 125I-protein A is added. The bound protein A is detected by autoradiography after the plates are exposed to Kodak XAR x-ray film (Eastman Kodak Company, Rochester, N.Y.) at −70° C. for 6–24 hours.

EXAMPLE X

METHODS FOR DETECTING CHRONIC MYELOGENOUS LEUKEMIA CELLS

Monoclonal antibodies against CML-G2 can be utilized to detect the presence of cells expressing CML-G2. Cells from peripheral blood or bone marrow are incubated with properly diluted monoclonal antibodies and reacted with fluoresceintagged rabbit antibodies against mouse antibodies. The monoclonal antibodies will bind specifically to CML-G2 expressing cells, which will in turn become fluorescently tagged.

The cells expressing CML-G2 are detected, for example, through a fluorescence microscope and the number of positive cells quantitated. Semi-quantitative estimation of antigens on cells can be obtained by subjecting cells to analysis by a fluorescence-activated cell sorter.

EXAMPLE XI

THERAPEUTIC TREATMENT OF CHRONIC MYELOGENOUS LEUKEMIA

Patients determined to have CML are treated with antibodies reactive with CML-G2 according to the method of Houghton, 1985, PNAS 82:1242, which is incorporated by reference. The antibodies are administered by infusion directly into the peripheral blood, or alternatively, through intramuscular or interperitoneal administration or the like. The antibodies are carried in a physiologically acceptable solution such as PBS. The effective dosage is determined from the weight of the patient and is generally between about 0.1 mg/kg and about 5 mg/kg body weight. Treatment is repeated at intervals as necessary to effect treatment.

EXAMPLE XII

THERAPEUTIC TREATMENT WITH ANTIBODY-TOXIN CONJUGATE

Patients determined to have CML are treated with CML-G2-specific antibodies conjugated with a toxin, by the method of Bumol, 1983, PNAS 80:529, which is incorporated by reference. Briefly monoclonal antibodies reacting with CML-G2 are prepared by conventional and well-known means, such as those detailed in Example VIII. The antibodies are purified and combined with excess (6 mol/mol) N-succinimydyl 3-(2-pyridyldithio) proprionate (Pharmacia, Uppsala, Sweden) in PBS (Pi/NaCl). After 30 minutes incubation at room temperature, the solution is dialyzed against Pi/NaCl. The modified antibodies are conjugated with an appropriate toxin, such as diptheria toxin A chain. Other toxins such as ricin A can also be employed. The diptheria toxin A chain is isolated as detailed in Bumol, supra, incorporated by reference. The modified antibodies are mixed with excess (3 mol/mol) reduced diptheria toxin A chain (10% of the total volume), allowed to react for 36 hours at 4° C., and concentrated with Sephadex G-200. The product is applied to a Sephadex G-200 column (1.0×100 cm), allowed to equilibrate and eluted with Pi/NaCl.

The toxin-conjugated antibodies are administered to the patient, preferably by intra-peritoneal injections of approximately 40 µg of purified antibody conjugate or as determined to be appropriate on the basis of patient weight, severity of tumor and other such factors. Injections are repeated at intervals, preferably approximately every three days.

It will be appreciated from the foregoing that the present invention provides a novel carbohydrate specific to CML granulocytes. It is thus a specific quantitative marker for CML and has utility including, but not limited to, diagnosis and therapy of CML. While the invention has been described with reference to specific examples, it will be appreciated that modifications can be made without departing from the spirit of the invention. The invention is limited therefore only by the following claims.

We claim:

1. An essentially pure carbohydrate having the following structure:

NeuNAcα2 ⟶ 3Galβ1 ⟶ 4GlcNAcβ1 ⟶

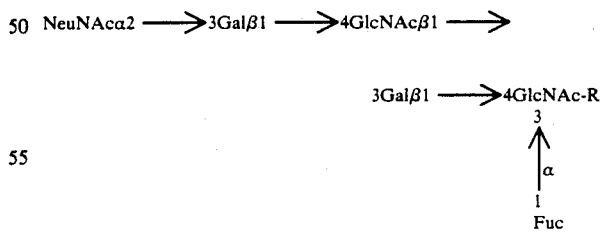

wherein R=1→3Galβ1→4Glcβ1→1Cer or H, said carbohydrate having no fucose attached to the subterminal N-acetyl glucosamine.

2. A purified antibody which specifically binds to the carbohydrate of claim 1.

3. A composition comprising: antibodies obtained by means of an immunologic response to exposure to a carbohydrate having the following structure:

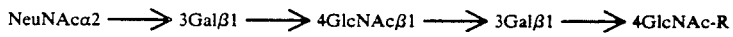
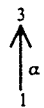

Fuc wherein R=1→3Galβ1→4Glcβ1→1Cer or H,
said carbohydrate having no fucose attached to the subterminal N-acetyl glucosamine.

4. The composition of claim 3 wherein said antibodies are polyclonal.

5. The composition of claim 3 wherein said antibodies are monoclonal.

6. A composition comprising: antibodies reactive with a carbohydrate having the following structure:

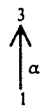

Fuc wherein R=1→3Galβ1→4Glcβ1→1Cer or H,
said carbohydrate having no fucose attached to the subterminal N-acetyl glucosamine, and said antibodies being conjugated to a cytotoxic agent.

7. The composition of claim 6, wherein the cytotoxic agent is a toxin.

8. The composition of claim 7 wherein said toxin is diptheria toxin A chain.

9. The composition of claim 7 wherein said toxin is ricin.

10. A composition comprising carbohydrate binding protein which binds specifically to the carbohydrate of claim 1 and a pharmaceutically acceptable Carrier.

11. The composition of claim 10 wherein said carbohydrate binding protein is a lectin.

12. A therapeutic method of treating a patient having chronic myelogenous leukemia, comprising the steps of:
providing a therapeutically effective amount of antibodies reactive with the carbohydrate of claim 1; and
introducing said antibodies into the patient.

13. A therapeutic method of treating patients having chronic myelogenous leukemia, comprising the steps of:
providing a therapeutically effective amount of antibodies reactive with a carbohydrate having the following structure:

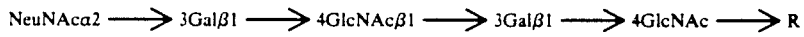
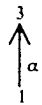

Fuc wherein R=1→3Galβ1→4Galβ1→1Cer or H,
said carbohydrate having no fucose attached to the subterminal N-acetyl glucosamine; and conjugating said antibodies to a toxin to form toxin conjugated antibodies;
introducing said toxin-conjugated antibodies into the patient.

14. The therapeutic method of claim 13 wherein said toxin is diptheria toxin A chain.

15. The therapeutic method of claim 13 wherein said toxin is ricin.

16. A method of therapeutically treating tumor cells having the carbohydrate of claim 1 which comprises contacting said tumor cells with a therapeutically effective amount of antibodies reactive with said carbohydrate wherein said antibodies are conjugated to a cytotoxic agent.

17. A diagnostic method for determining the presence of chronic myelogenous leukemia in a human patient comprising the steps of:
a. combining a sample of the human patient's body fluid or cells with antibodies specific to a carbohydrate having the following structure:

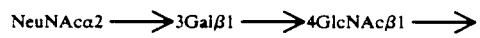
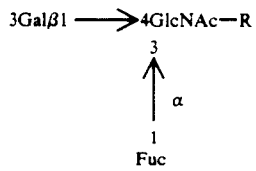

wherein R=1→3Galβ1→4Glcβ1→1Cer or H,
said carbohydrate having no fucose attached to the subterminal N-acetyl glucosamine; and
b. monitoring the result of step (a) to determine whether said antibodies have bound to said carbohydrate in an immunological reaction, thereby indicating that said patient has chronic myelogenous leukemia.

* * * * *

UNITED STATES PATENT AND TRADEMARK OFFICE
CERTIFICATE OF CORRECTION

PATENT NO. : 4,939,083

DATED : July 3, 1990

INVENTOR(S) : Fukuda et al.

It is certified that error appears in the above-identified patent and that said Letters Patent is hereby corrected as shown below:

In column 4, line 4, delete "1→3Galβ1→5GLcβ1→1Cer" and insert therefor --1→3Galβ1→4Glcβ1→1Cer--.

In column 4, line 68, delete "985" and insert therefor --1985--.

In column 5, line 48, delete "NH4OH" and insert therefor --$NH_4OH$--.

In column 5, line 50, delete "G2" and insert therefor --$G_2$--.

In column 6, line 40, delete "G2" and insert therefor --$G_2$--.

In column 6, line 46, delete "HexNAc2+" and insert therefor --$HexNAc_2^+$--.

In column 6, line 47, delete "Hex.HexNAc." and insert therefor --Hex.HexNAc+--.

In column 6, line 53, delete "HexNAo" and insert therefor --HexNAc--.

In column 7, line 23, delete "G2" and insert therefor --$G_2$--.

In column 8, line 11, delete "92" and insert therefor --492--.

In column 8, line 62, delete "NH4" and insert therefor --$NH_4$--.

UNITED STATES PATENT AND TRADEMARK OFFICE
CERTIFICATE OF CORRECTION

PATENT NO. : 4,939,083

DATED : July 3, 1990

INVENTOR(S) : Fukuda et al.

It is certified that error appears in the above-identified patent and that said Letters Patent is hereby corrected as shown below:

In column 9, line 31, delete "fluoresceintagged" and insert therefor --fluorescein-tagged--.

Signed and Sealed this

Third Day of March, 1992

Attest:

HARRY F. MANBECK, JR.

*Attesting Officer*      *Commissioner of Patents and Trademarks*